United States Patent
Melapudi et al.

(10) Patent No.: US 12,056,871 B2
(45) Date of Patent: Aug. 6, 2024

(54) METHOD AND SYSTEM FOR MANAGING IMAGE QUALITY UTILIZING A GENERATIVE MODEL

(71) Applicant: GE Precision Healthcare LLC, Wauwatosa, WI (US)

(72) Inventors: Vikram Melapudi, Bangalore (IN); Rahul Venkataramani, Bangalore (IN)

(73) Assignee: GE Precision Healthcare LLC, Wauwatosa, WI (US)

(*) Notice: Subject to any disclaimer, the term of this patent is extended or adjusted under 35 U.S.C. 154(b) by 396 days.

(21) Appl. No.: 17/242,156

(22) Filed: Apr. 27, 2021

(65) Prior Publication Data

US 2021/0350531 A1   Nov. 11, 2021

(30) Foreign Application Priority Data

May 8, 2020   (IN) .............................. 202041019511

(51) Int. Cl.
| | |
|---|---|
| *A61B 8/08* | (2006.01) |
| *A61B 8/00* | (2006.01) |
| *G06N 3/08* | (2023.01) |
| *G06T 7/00* | (2017.01) |

(52) U.S. Cl.
CPC ............ *G06T 7/0012* (2013.01); *A61B 8/461* (2013.01); *A61B 8/5269* (2013.01); *G06N 3/08* (2013.01); *G06T 2207/10132* (2013.01)

(58) Field of Classification Search
CPC ..... A61B 8/0866; A61B 8/461; A61B 8/5207; A61B 8/523; A61B 8/5269; A61B 8/54; G06N 3/045; G06N 3/08; G06T 2207/10132; G06T 7/0012
See application file for complete search history.

(56) References Cited

U.S. PATENT DOCUMENTS

| | | | |
|---|---|---|---|
| 11,138,731 B2* | 10/2021 | Katzmann | G06T 7/0014 |
| 11,501,438 B2* | 11/2022 | Xu | G06N 3/048 |
| 2018/0042577 A1* | 2/2018 | Perrey | A61B 8/085 |
| 2019/0282208 A1 | 9/2019 | Silberman | |
| 2019/0333219 A1* | 10/2019 | Xu | G06N 3/047 |
| 2019/0370969 A1* | 12/2019 | Katzmann | G06N 3/047 |
| 2020/0074664 A1* | 3/2020 | Weber | G06T 17/00 |
| 2020/0202502 A1* | 6/2020 | Tsymbalenko | G06T 5/60 |
| 2021/0350531 A1* | 11/2021 | Melapudi | G06T 7/0012 |

FOREIGN PATENT DOCUMENTS

| | | | |
|---|---|---|---|
| WO | WO-2018209140 A1 * | 11/2018 | ........... A61B 5/0095 |
| WO | 2019238804 A1 | 12/2019 | |

* cited by examiner

*Primary Examiner* — Tsung Yin Tsai

(57) ABSTRACT

Systems, methods and computer program products are provided to collect ultrasound (US) data. A processor is configured to acquire the US data along one or more acquisition scan planes. The US data defines a plurality of image frames that have a first image quality. The processor is further configured to apply a generative model to at least one of the US data or plurality of image frames to generate a synthetic scan plane image along a synthetic scan plane. The generative model is defined based on one or more training ultrasound data sets. The synthetic scan plane image has an image quality that is common with the first image quality of the plurality of image frames. The system further comprises a display configured to display the synthetic scan plane image.

21 Claims, 9 Drawing Sheets

Image selection from time sequence volume of images by moving the probe

Liver, kidney

Liver, GB

METHOD AND SYSTEM FOR MANAGING IMAGE QUALITY UTILIZING A GENERATIVE MODEL

FIELD

Aspects of the present disclosure relate to medical imaging. More specifically, certain embodiments relate to methods and systems that utilize generative models to facilitate a diagnostic ultrasound imaging workflow.

BACKGROUND OF THE INVENTION

Ultrasound imaging has been employed for a wide variety of applications. During the process of ultrasound scanning, a clinician attempts to capture a view of a certain anatomy which confirms/negates a particular medical condition. Once the clinician is satisfied with the quality of the view and/or the scan plane, the image is selected to proceed to the measurement phase. For example, ultrasound images are routinely used to assess gestational age (GA) and weight of a fetus or to monitor cardiac health of a patient. Ultrasound measurements of specific features of fetal anatomy such as the head, abdomen or the femur from two-dimensional (2D) or three-dimensional (3D) image data are used in the determination of GA, assessment of growth patterns and identification of anomalies. Similarly, for cardiac applications, thicknesses of cardiac walls are routinely measured by cardiologists to check for cardiomyopathy.

Usually the user acquires a sequence of images along different scan planes and then chooses the best scan plane and image to provide the remarks, evaluate or perform biometry. The process of selecting the best scan plane and image can also be performed offline, such as from a stored sequence of images (cine loop) or volume of slices (acquired using a 3D probe). Image acquisition is challenging. Currently, image acquisition takes anywhere between 1 to 5 minutes for each correct scan plane acquisition and more so for novice clinicians. The other challenge the less experienced clinicians/sonographers face is the ability to correctly identify acceptable scan planes. It is also desirable for the clinicians to have an understanding of how far they are from a correct or "best" scan plane for a particular feature of interest. Moreover, ultrasound images are subject to both patient and operator/clinician variability. Also, determining a quality of an image is fraught with challenges. Particularly, pixel intensities in the images vary significantly with different gain settings.

Currently, there exist semi-automated and automated techniques for ultrasound image analysis. However, ultrasound images, such as fetal ultrasound images, suffer from a number of factors that can compromise image quality and diagnosis. Ultrasound (US) image quality is dependent on several factors such as user expertise, acquisition quality, patient cooperation, device settings, anatomy evaluated, near field haze due to fat deposits, speckle noise, the weight/degree of obesity of the subject, and the like.

Operator variability also limits reproducibility of particular image frames and measurement. There are multiple reasons for the inter-operator variability. Firstly, two-dimensional (2D) echocardiography visualizes only a cross-sectional slice of a three-dimensional structure, commonly referred to as the scan plane. Even small changes in positioning of the transducer, which has six degrees of freedom, may lead to significant changes in the scene visualized, which may in turn lead to incorrect measurement. In addition, sub-optimal ultrasound image settings such as gain, time-gain compensation may decrease the ability to visualize the internal structures of the human body.

Heretofore, a common problem in ultrasound scanning is the difficulty in identifying a preferred/optimal scan plane image to be utilized in connection with a particular examination or analysis, along with a preferred/optimal set of values for scan acquisition parameters. The preferred/optimal scan plane image depends at least in part on acquisition quality and varies widely across different 3-D volumes or cine loops. A specification of how to choose a single scan plane image from a sequence should consider the image quality at hand and make suitable concessions in evaluation and comparison between available scan plane images.

Non-standard image quality implies that the guidelines could be manifest in multiple non-standard ways and operators typically have to use subjective judgment and rely on prior experience. The challenges are faced by both human and algorithmic approaches towards selecting optimal scan plane images. Given that US images exhibit non-standard quality, the evaluation of an image or selecting a "best" scan plane and image requires a user to consider different aspects, affecting quality, that are not possible to quantify, measure or control. Hence the final scan quality is heavily dependent on the user's expertise and experience level.

In the past, algorithms have been proposed to assist in selection of a preferred scan plane image. However, conventional algorithmic approaches also experience problems due to nonstandard image quality. For example, conventional algorithmic approaches typically utilize an average, that is obtained across multiple training images, for one or more parameters. The conventional algorithmic approaches are only as accurate as the average for the training images utilized to develop the algorithms.

Additional limitations and disadvantages of conventional and traditional approaches will become apparent to one of skill in the art, through comparison of such systems with some aspects of the present disclosure, as set forth in the remainder of the present application with reference to the drawings.

BRIEF DESCRIPTION

In accordance with new and unique aspects herein, methods and systems utilize a generative model, such as a generative adversarial network (GAN) based approach to generate a representative or ideal scan plane image. The generated image would be of similar quality to the acquisition image frames and hence serves as an adaptable scan plane image that can be used as reference point by user or algorithms. Further, the difference between the generated synthetic scan plane image and current acquisition image frame can be used to develop a quality score, guide user action, tune acquisition settings and provide explanation on quality of the current acquisition image frame.

In accordance with new and unique aspects herein, the methods and systems are configured to generate a synthetic scan plane image that is similar in image quality to the image frames being acquired or reviewed. The synthetic scan plane image is generated from a subset of the image frames that are acquired, for example, 2-100 image frames, or preferably 2-50 image frames, or more preferably 5-20 image frames. The synthetic scan plane image is adaptable as it is re-generated each time a new plurality of image frames is acquired.

In accordance with new and unique aspects herein, the methods and systems present the synthetic scan plane image synthetic scan plane image to a user and support the user to enable circumvention of the challenges of non-standard image quality in US evaluation. The synthetic scan plane image is displayed to novice or nonexpert users which helps improve the diagnosis accuracy and is displayed to expert users which helps accelerate the workflow.

In accordance with new and unique aspects herein, the methods and systems avoid limiting an accuracy of the generative model to an average of the training set. The methods and systems do so by actively learn and incorporate image quality factors in connection with generating a reference scan plane image for a given subject, thereby overcoming challenges due to non-standard image quality.

The methods and systems herein provide an automated manner for identifying a synthetic scan plane which afford advantages over human operators. Among other advantages, the automated methods and systems herein guide novice users to understand termination criteria for a scanning session or alert users to the necessity to change settings to obtain a desirable scan plane. Additionally or alternatively, the automated methods and systems herein accelerate workflow for expert users. The methods and systems herein afford an automated process for obtaining the optimal scan plane through the following: i) provide a quality score of acquisition or protocol completeness, ii) provide guidance or automatically tune acquisition settings, iii) provide probe guidance, iv) provide explanations for why the reference scan plane is preferred and optionally provide quality scores to measure user required scan planes relative to a reference scan plane.

In accordance with embodiments herein, an anomaly-GAN is utilized as a framework to provide the best possible synthetic scan plane image accounting for the variation in image quality for the user or the algorithm to make the selection of the slice image. In addition, the availability of such a synthetic scan plane image enables providing additional information like real-time acquisition quality, protocol completeness, guidance for acquisition settings, explainability and probe manipulation. The proposed solution leverages the ability of GAN to produce reference (non-anomalous) images of the same general image quality and hence provide an adaptable synthetic scan plane image for the algorithm's or user's action. In accordance with embodiments herein, a system is provided. The system comprises a transducer with piezoelectric transducer elements configured to collect ultrasound (US) data; memory configured to store program instructions; and a processor configured to acquire the US data, utilizing the transducer elements, along one or more acquisition scan planes, the US data defining a plurality of image frames that have a first image quality. The processor is further configured to apply a generative model to at least one of the US data or plurality of image frames to generate a synthetic scan plane image along a synthetic scan plane, wherein the generative model is defined based on one or more training ultrasound data sets, the synthetic scan plane image having an image quality that is common with the first image quality of the plurality of image frames. The system further comprises a display configured to display the synthetic scan plane image.

Additionally or alternatively, the processor is further configured to predict the synthetic scan plane image based on a generative adversarial network model. Additionally or alternatively, the synthetic scan plane image does not correspond to any scan planes associated with any of the plurality of acquisition image frames. Additionally or alternatively, color the processor is further configured to repeat the acquire and apply to adaptively identify a new synthetic scan plane image based on new acquisition image frames image frames. Additionally or alternatively, the generative model applies acquisition parameters to identify the synthetic scan plane image. Additionally or alternatively, the processor is further configured to provide user guidance information to change gain or other scan acquisition parameter based on differences between the synthetic scan plane image and the plurality of image frames. Additionally or alternatively, the processor is further configured to provide user guidance information regarding at least one of position or orientation information for a scan plane for a future image frame to be acquired. Additionally or alternatively, the processor is implemented in at least one of an ultrasound system, a smart phone, tablet device, laptop computer, desktop computer or server.

In accordance with embodiments herein, a method is provided that comprises: utilizing a transducer to transmit ultrasound signals and receive ultrasound (US) data from a region of interest, wherein the US data is acquired along one or more acquisition scan planes, the US data defining a plurality of image frames that have a first image quality; applying a generative model to at least one of the US data or plurality of image frames to generate a synthetic scan plane image along a synthetic scan plane, wherein the generative model is defined based on one or more training ultrasound data sets, the synthetic scan plane image having an image quality that is common with the first image quality of the plurality of image frames; and displaying the synthetic scan plane image.

Additionally or alternatively, the method further includes predicting the synthetic scan plane image based on a generative adversarial network model. Additionally or alternatively the synthetic scan plane image does not correspond to any scan planes associated with any of the plurality of acquisition image frames. Additionally or alternatively, the method repeats the acquiring and the applying to adaptively identify a new synthetic scan plane image based on new acquisition image frames image frames. Additionally or alternatively, the method further comprises providing user guidance information to change gain or other scan acquisition parameter based on differences between the synthetic scan plane image and the plurality of image frames. Additionally or alternatively, the method further comprises obtaining a reference scan plane image, from a reference library, to the generative model and utilizing the reference scan plane image to generate the synthetic scan plane image with the image quality of the synthetic scan plane image being common with a quality of the reference scan plane image. Additionally or alternatively, the common image quality is defined by at least a first quality characteristic, the method further comprising defining a tolerance range for the first quality characteristic based on a variation of the first quality characteristic across the plurality of image frames, the generative model providing the reference frame with the first quality characteristic within the tolerance range.

In accordance with new and unique aspects herein, diagnostic information is not derived directly from the synthetic scan plane, the diagnostic information derived from the plurality of image frames.

In accordance with embodiments herein, a computer program product is provided that comprises a non-signal computer readable storage medium comprising computer executable code to: obtain ultrasound (US) data from a region of interest, wherein the US data is acquired along one or more acquisition scan planes, the US data defining a plurality of image frames that have a first image quality; apply a generative model to at least one of the US data or plurality of image frames to generate a synthetic scan plane image along a synthetic scan plane, wherein the generative model is defined based on one or more training ultrasound data sets, the synthetic scan plane image having an image quality that is common with the first image quality of the plurality of image frames; and display the synthetic scan plane image.

Additionally or alternatively, the computer executable code is further configured to apply includes predicting the synthetic scan plane image based on a generative adversarial network model. Additionally or alternatively, the common image quality is defined by at least a first quality characteristic and wherein the computer executable code is further configured to define a tolerance range for the first quality characteristic based on a variation of the first quality characteristic across the plurality of image frames, the generative model providing the reference frame with the first quality characteristic within the tolerance range. Additionally or alternatively, the computer executable code is further configured to provide user guidance information to at least one of: i) change gain or other scan acquisition parameter based on differences between the synthetic scan plane image and the plurality of image frames; or ii) at least one of position or orientation information for a scan plane for a future image frame to be acquired.

DETAILED DESCRIPTION

Figure 1:
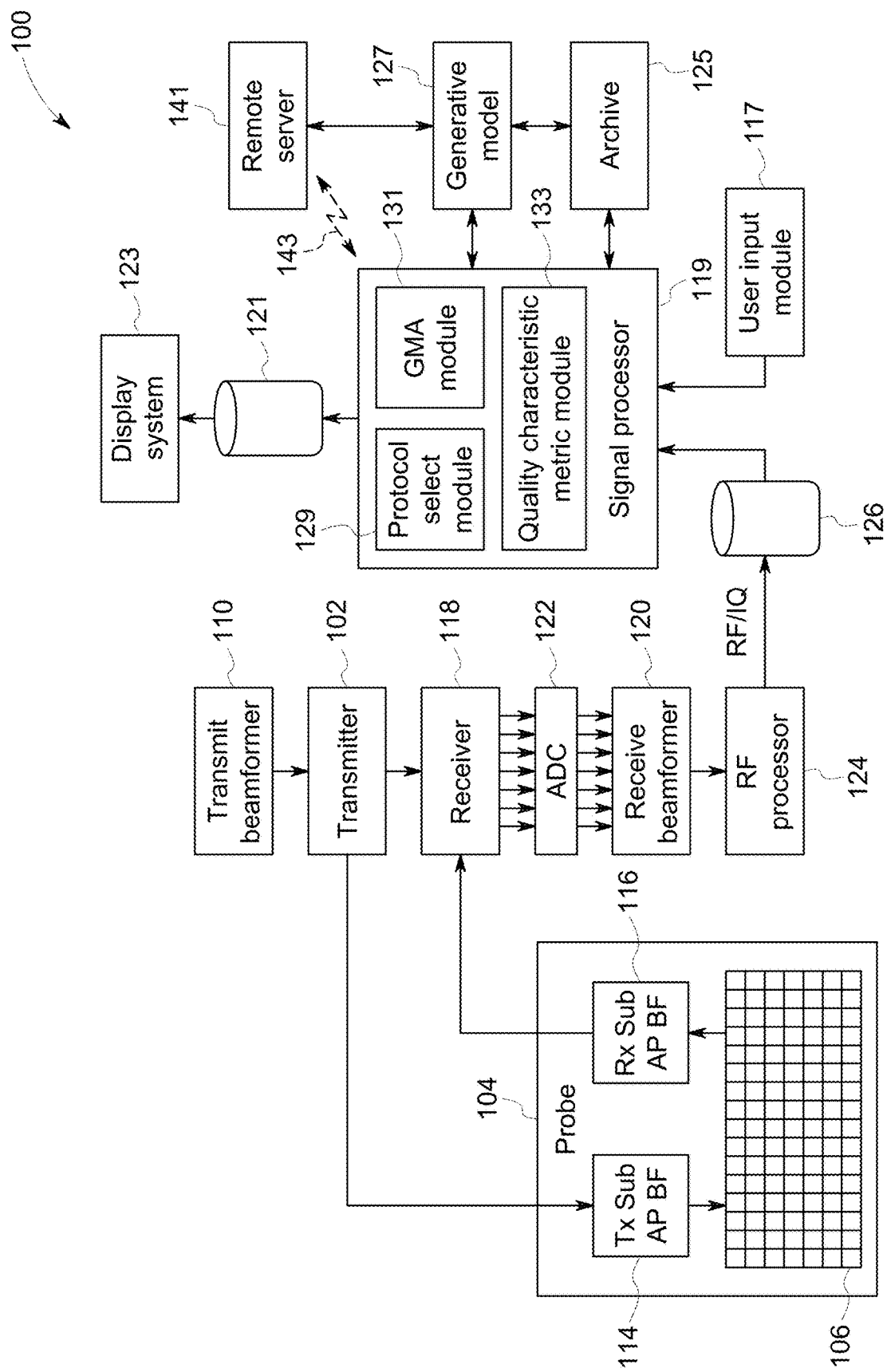
FIG. 1 illustrates an ultrasound system in accordance with embodiments herein.

The foregoing summary, as well as the following detailed description of certain embodiments will be better understood when read in conjunction with the appended drawings. To the extent that the Figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general-purpose signal processor or a block of random-access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized, and that structural, logical and electrical changes may be made without departing from the scope of the various embodiments. The following detailed description is, therefore, not to be taken in a limiting sense, and the scope of the present invention is defined by the appended claims and their equivalents.

As used herein, an element or step recited in the singular and proceeded with the word "a" or "an" should be understood as not excluding plural of said elements or steps, unless such exclusion is explicitly stated. Furthermore, references to "an embodiment," "one embodiment," "a representative embodiment," "an example embodiment," "various embodiments," "certain embodiments," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as three-dimensional (3D) mode, B-mode, CF-mode, and/or sub-modes of B-mode and/or CF such as Shear Wave Elasticity Imaging (SWEI), TVI, Angio, B-flow, BMI, BMI_Angio, and in some cases also MM, CM, μW, TVD, CW where the "image" and/or "plane" includes a single beam or multiple beams.

The term processor or processing unit, as used herein, refers to any type of processing unit that can carry out the required calculations needed for the various embodiments, such as single or multi-core: CPU, Graphics Board, DSP, FPGA, ASIC or a combination thereof.

The term "scan plane" shall mean a plane along which ultrasound data is acquired during a scanning operation, with the plane being defined through six of freedom relative to a reference coordinate system. The scan plane has a given position and orientation within the coordinate system.

The term "image frame" shall refer to an image that can be or is or could be generated based on ultrasound data that is collected along a corresponding scan plane.

The term "acquisition scan plane" shall mean a scan plane defined by a position and orientation of a US probe within a reference coordinate system while the US probe is acquiring US data.

The terms "acquisition scan plane image" or "ASP image" shall mean an image frame defined by ultrasound data acquired from a region of interest along a corresponding acquisition scan plane.

The term "acquisition image frame" shall mean an image frame defined by US data that is acquired during a corresponding scanning session.

The term "generative model" shall mean a class of methods for learning generative models which are used to learn the distribution of a data in unsupervised fashion. The training details that make GANs peculiar are described herein. Nonlimiting examples of generative models include a generative adversarial network (GAN), a deep convolution (DC) GAN, conditional GAN, Pix2Pix, CycleGAN and the like. A goal of a generative model framework is to train a generative network that produces samples from a data distribution by transforming vectors of noise. A training signal for a generator network is provided by a discriminator network that is trained to distinguish samples from the generator distribution from real data. The generator network in-turn is entrained to fool the discriminator into accepting its output as being real. A GAN is one approach for training a generative model and includes a wide variety of architectures, such as GAN, Ano-GAN, Cycle-GAN, and the like. Non-limiting examples of other generative models include Hidden Markov Models (HMM), Gaussian mixture model (GMM), Bayesian networks, Boltzman machine and the like. Generative models, like GAN, produces an example data instance, from a distribution, given a quantification or qualification. The variation in sampling is achieved through the noise vector. GAN is a particular way of learning such generative models. For the avoidance of doubt, generative models are not discriminative machine learning models which qualify or quantify a given data set.

The term "synthetic scan plane" shall mean a scan plane defined by an estimated or theoretical position and orientation, at which an ultrasound probe could potentially be positioned within a reference coordinate system, wherein the estimated or theoretical scan plane is derived by a generative model.

The term "synthetic scan plane image" shall mean an estimated or theoretical image generated by the generative model based on the US data set and/or based on a plurality of image frames generated from the US data set, wherein the synthetic scan plane image represents an estimation or projection of a potential image frame that could be generated, if US data were acquired along the synthetic scan plane.

The terms "characteristic of quality" and "quality characteristic" are used interchangeably and shall mean a characteristic of image quality. Nonlimiting examples of quality characteristics include noise, artifacts, shadows, smearing, haze, blurring, and saturation.

The term "common image quality," when used in conjunction with comparing acquisition image frames and/or acquisition and synthetic scan plane images, shall mean that the acquisition image frames and/or acquisition and synthetic scan plane images have the same or similar (e.g., within 5%) levels or degrees for multiple characteristics that define quality. It is recognized that the level or degree for an individual characteristic of image quality will vary within a tolerance range while the characteristic is considered common or constant (e.g., +/−1% to 6%). For example, successive image frames in a cine loop or 3D volume may exhibit slight differences in a level of one or more quality characteristics but will still be considered to represent a common image quality. By way of example, the "common" level for a quality characteristic may be defined based on maximum and minimum levels for the quality characteristic exhibited across the image frames in a single cine loop and/or 3D volume. As a further example, a level of blurriness may vary for a small (5%) range between B1 and Bn for a collection of image frames in a single cine loop (or 3D volume), where the range B1 to Bn is defined to represent a "common" level of blurriness. Shadowing may vary over a small (+/−2.5%) range between S1 and Sn for a collection of image frames in a single cine loop (or 3D volume), where the range S1 to Sn is defined to represent a "common" level of shadowing.

The term "image quality" shall mean a degree or level of one or more characteristics of an image frame that effect or otherwise bear on an ability of physicians or other medical personnel to utilize the image frame in connection with a diagnostic examination of an anatomy of interest. Nonlimiting examples of characteristics that define image quality include a degree of blurriness, an extent of shadows, speckle, saturation, field of view, scan plane presentation/angle/orientation, size or completeness of anatomical structures, presence of necessary anatomical structures (e.g., a good quality TCP scan plane in fetal CNS evaluation requires presence of CSP, CP, symmetric cerebellum, complete head circumference).

FIG. 1 is a block diagram of an exemplary ultrasound system 100 that is operable to collect, analyze, display and otherwise process ultrasound data in accordance with embodiments herein. The ultrasound system 100 comprises a transmitter 102, an ultrasound probe 104, a transmit beamformer 110, a receiver 118, a receive beamformer 120, a RF processor 124, a RF/IQ buffer 126, a user input module 117, a signal processor 119, an image buffer 121, a display system 123, an archive 125, and a generative model 127.

The transmitter 102 may comprise suitable logic, circuitry, interfaces and/or code that may be operable to drive an ultrasound probe 104. The ultrasound probe 104 may be constructed in various forms with various configurations of transducer elements 106, ranging between various types of one-dimensional and two-dimensional arrays. The transmitter and the ultrasound probe may be implemented and/or configured for one-dimensional (1D), two-dimensional (2D), three-dimensional (3D), and/or four-dimensional (4D) ultrasound scanning. The ultrasound probe may comprise a one-dimensional (1D, 1.25D, 1.5D or 1.75D) array or a two-dimensional (2D) array of piezoelectric elements. The ultrasound probe may comprise a group of transmit transducer elements and a group of receive transducer elements, that normally constitute the same elements. The transmitter may be driven by the transmit beamformer. The transmit beamformer may comprise suitable circuitry that may be operable to control the transmitter which, through a transmit sub-aperture beamformer, drives the group of transmit transducer elements to emit ultrasonic transmit signals into a region of interest (e.g., human, animal, underground cavity, physical structure and the like).

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 106.

The receive transducer elements 106 convert the received echoes into analog signals may undergo sub-aperture beamforming by a receive sub-aperture beamformer 116 and are then communicated to a receiver 118. The receiver 118 may comprise suitable logic, circuitry, interfaces and/or code that may be operable to receive and demodulate the signals from the receive sub-aperture beamformer 116. The demodulated analog signals may be communicated to one or more of the plurality of A/D converters 122.

The plurality of A/D converters 122 may comprise suitable logic, circuitry, interfaces and/or code that may be operable to convert the demodulated analog signals from the receiver 118 to corresponding digital signals. The plurality of A/D converters 122 are disposed between the receiver 118 and the receive beamformer 120. Notwithstanding, the disclosure is not limited in this regard. Accordingly, in some embodiments, the plurality of A/D converters 122 may be integrated within the receiver 118.

The receive beamformer 120 may comprise suitable logic, circuitry, interfaces and/or code that may be operable to perform digital beamforming processing to, for example, sum the delayed channel signals received from the plurality of A/D converters 122 and output a beam summed signal. The resulting processed information may be converted back to corresponding RF signals. The corresponding output RF signals that are output from the receive beamformer 120 may be communicated to the RF processor 124. In accordance with some embodiments, the receiver 118, the plurality of A/D converters 122, and the beamformer 120 may be integrated into a single beamformer, which may be digital.

The RF processor 124 may comprise suitable logic, circuitry, interfaces and/or code that may be operable to demodulate the RF signals. In accordance with an embodiment, the RF processor 124 may comprise a complex demodulator (not shown) that is operable to demodulate the RF signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124. The RF/IQ buffer 126 and/or image buffer 121 may represent one or more memory configured to store two-dimensional (2D) and/or three-dimensional (3D) datasets of the ultrasound data, where such datasets are accessed to present 2D and/or 3D images. Multiple consecutive 3D datasets may also be acquired and stored over time, such as to provide real-time 3D or four-dimensional (4D) display. The images may be modified and the display settings of the display 123 also manually adjusted using the user interface 117.

The user input module 117 may be utilized to input patient data, scan parameters, settings, select protocols and/or templates, navigate image loop viewing, and the like. In an exemplary embodiment, the user input module 117 may be operable to configure, manage and/or control operation of one or more components and/or modules in the ultrasound system 100. In this regard, the user input module 117 may be operable to configure, manage and/or control operation of the transmitter 102, the ultrasound probe 104, the transmit beamformer 110, the receiver 118, the receive beamformer 120, the RF processor 124, the RF/IQ buffer 126, the user input module 117, the signal processor 119, the image buffer 121, the display system 123, the archive 125, and/or the generative model 127. The user input module 117 may include button(s), a touchscreen, motion tracking, voice recognition, a mouse-based device, keyboard, camera and/or any other device capable of receiving a user directive. In certain embodiments, one or more of the user input modules 117 may be integrated into other components, such as the display system 123, for example. As an example, user input module 117 may include a touchscreen display. In various embodiments, an ultrasound image presented at the display system 123 may be manipulated to zoom in and/or out in response to a directive received via the user input module 117.

The signal processor 119 may comprise suitable logic, circuitry, interfaces and/or code that may be operable to process ultrasound scan data (i.e., RF signal data or IQ data pairs) for generating ultrasound images for presentation on a display system 123. The signal processor 119 is operable to perform one or more processing operations according to a plurality of selectable ultrasound modalities on the acquired ultrasound scan data. In an exemplary embodiment, the signal processor 119 may be operable to perform compounding, motion tracking, and/or speckle tracking. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation. The processed image data can be presented at the display system 123 and/or may be stored at the archive 125. The archive 125 may be a local archive, a Picture Archiving and Communication System (PACS), or any suitable device for storing images and related information. In the exemplary embodiment, the signal processor 119 may comprise a protocol selection module 129, an image intake module 150, an image loop view assignment module 160, and an image characteristic metric assignment module 170.

The ultrasound system 100 may be operable to acquire ultrasound scan data at a frame rate that is suitable for the imaging situation in question. Typical frame rates range from 20-70 but may be lower or higher. The acquired ultrasound scan data may be displayed on the display system 123 at a display-rate that can be the same as the frame rate, or slower or faster. An image buffer 121 is included for storing processed frames of acquired ultrasound scan data that are not scheduled to be displayed immediately. Preferably, the image buffer 121 is of sufficient capacity to store at least several minutes' worth of frames of ultrasound scan data. The frames of ultrasound scan data are stored in a manner to facilitate retrieval thereof according to its order or time of acquisition. The image buffer 121 may be embodied as any known data storage medium.

The signal processor 119 may include a protocol selection module 129 that comprises suitable logic, circuitry, interfaces and/or code that may be operable to configure the parameters associated with image acquisition and processing in response to user instructions provided at the user input module 117. For example, the protocol selection module 129 may receive a user input selecting a protocol and/or template defining a set of acquisition and/or processing parameters. As another example, the protocol selection module 129 may receive a user input selecting individual acquisition and/or processing parameters. In various embodiments, the selected protocol, template, and/or individual parameters may define the number of heart cycles per image loop and the desired image view types, among other things. For example, the number of heart cycles per image loop is typically one heart cycle per loop, but could be set at two cycles, three cycles, or any suitable number of cycles. Examples of image view types may include a parasternal long axis (PLAX) view, a parasternal short axis on mitral (SAX-MV) view, a four chamber (4CH) view, a two chamber (2CH) view, an apical long axis/3-chamber (APLAX) view, a parasternal short axis on papillary muscle (SAX-PM) view, or any suitable image view type. In a representative embodiment, the selected image acquisition and processing parameters may be stored for retrieval and application by the signal processor 119 and its associated modules during ultrasound image acquisition and processing. For example, the parameters may be stored in archive 125 or any suitable data storage medium. In an exemplary embodiment, the protocol selection module 129 may apply a default protocol or template of default acquisition and processing parameters if the parameters are not defined or changed by user instructions provided via the user input module 117.

The signal processor 119 may include a generative model application (GMA) module 131 that comprises suitable logic, circuitry, interfaces and/or code that may be operable to automatically assign an image view type to at least a portion of the image loops. The GMA module 131 may be operable to build, update and manage generative models 127. Optionally, a separate computing device, such as a separate smart phone, tablet device, workstation, laptop computer, remote server, medical network computing system and the like may be utilized to build, update and manage the generative models 127. For example, additionally or alternatively, a remote server 141 may be included in the system. The remote server 141 may include memory and processors configured to implement the GMA module 131. The GMA module 131 applies training ultrasound data sets to build corresponding generative models, such as to build GAN models. Examples are discussed herein for manners in which the generative models may be constructed and maintained.

The GMA module 131 is further configured to manage application of one or more generative models to the ultrasound data and/or a plurality of image frames to generate one or more synthetic scan plane images along corresponding one or more synthetic scan planes. The GMA module 131 may be configured to predict the synthetic scan plane image based on a generative adversarial network. As explained herein, the synthetic scan plane image does not correspond to a scan plane of any of the plurality of acquisition image frames generated based on the US data set. Instead, the synthetic scan plane image represents an estimation or projection of a potential image frame that could be generated from the potential ultrasound data if the potential ultrasound data were acquired along an actual scan plane matching the synthetic scan plane. It should be recognized that a synthetic scan plane image is not suited for, and is not utilized to, acquire measurements or any other diagnostic information. Diagnostic information, including measurements and other information, is not derived directly from the synthetic scan plane image. Instead, the diagnostic information, including measurements and other information, are derived from the plurality of acquisition image frames.

Additionally or alternatively, the signal processor 119 may be configured to repeat management of the acquisition of additional US data sets and the GMA module 131 may be further configured to repeat the application of the generative model to each new US data set in order to adaptively identify new synthetic scan plane images based on the new acquisition image frames.

The generative model applies various acquisition parameters, as explained herein, to identify the synthetic scan plane image. In a simple implementation, the GMA module 131 applies a common generative model 127 in connection with all ultrasound examinations. Additionally or alternatively, when multiple generative models 127 are available, the GMA module 131 first determines the protocol to be utilized from the protocol selection module 129. Based on the protocol, patient demographics and other information, the GMA module 131 selects one of the generative models 127. The GMA module 131 may implement various types of generative models 127, such as a generative adversarial network. For example, the generative model 127 may comprise an input layer, an output layer, and one or more hidden layers in between the input and output layers. Each of the layers may be made up of a plurality of processing nodes that may be referred to as neurons. For example, the input layer may have a neuron for each pixel or a group of pixels from an image loop. The output layer may have a neuron corresponding to each image view type plus a neuron corresponding to an unknown or other image view type that does not match one of the predefined image view types.

The generative models 127 may include various types of generative models. For example, a separate generative model 127 may be defined in connection with each type of examination protocol. Additionally or alternatively, separate generative models 127 may be defined in connection with different patient anatomies, different ultrasound probes, different patient demographics and the like. For example, first and second generative models 127 may be defined for a kidney examination protocol, where the first generative model 127 is utilized for thin patients or adolescence, while the second generative model 127 is utilized for the obese patients or adults. As another example, different generative models 127 may be defined in connection with different levels of user experience.

For example, a first generative model 127 may be utilized with inexperienced users, while a second generative model 127 may be utilized with more experienced users. It may be desirable to utilize different generative models with users having different levels of experience to allow for different tolerance ranges or levels of criticality to be applied. For example, an inexperienced user may not be able to achieve a particular acquisition scan plane image, and thus the corresponding generative model may be constructed to provide a less specific final acquisition scan plane image. Alternatively, an experienced user should be able to achieve a particular acquisition scan plane image and thus a "more critical" generative model may be utilized to guide the experienced user. As another example, generative models utilized with experienced users may analyze fewer image quality characteristics, namely only quality characteristics that experienced users still struggle with, while not considering image characteristics that experienced users have proven to be quite good at achieving high quality. Alternatively, generative models used within experienced users may analyze a broader range of quality characteristics, such as to provide a backup check on a broader range of settings and characteristics.

The generative models are configured to output a synthetic scan plane image based on an input ultrasound data set and/or set of image frames, where the synthetic scan plane image has an image quality that is common with the image quality of the plurality of image frames.

In accordance with some embodiments, the generative models 127 are maintained in memory within the ultrasound system or locally (e.g., in a near-by storage unit, server). Additionally or alternatively, the generative models 127 may be maintained remotely in memory at the remote server 141. When the generative models 127 are maintained at a remote server 141, the remote server 141 and the local ultrasound system 100 may communicate over a wired or wireless communications network (as figuratively denoted by the dashed line 143). For example, the remote server 141 may periodically push new or updated generative models to the ultrasound system 100. Additionally or alternatively, the ultrasound system 100 may convey a model request to the remote server 141 with certain information (e.g., a protocol for an upcoming scan, demographics of the patient, scan acquisition settings, the type of probe to be utilized, a model/version of the ultrasound system, etc.) associated with designating a particular type of generative model. In response to the model request, the remote server 141 may send one or more generative models 127 to the ultrasound system 100.

The signal processor 119 may include a quality characteristic metric (QCM) module 133 that comprises suitable logic, circuitry, interfaces and/or code that may be operable to automatically assign values or levels to one or more quality characteristics of the synthetic scan plane image(s) and the acquisition image frames. For example, the QCM module 133 may assign levels to quality characteristics in connection with one or more of noise, artifacts, shadows, smearing, haze, blurring, saturation and the like. Once the levels are assigned, the QCM module 133 may determine whether a synthetic scan plane image has an image quality that is common with an image quality of one or more of the plurality of image frames. In accordance with embodiments herein, one or a subset of primary quality characteristic may be defined to be of interest in connection with certain types of protocols and/or certain scan planes. For example, in a fetal CNS examination protocol, a first quality characteristic related to shadowing may be of primary interest, and thus represent the primary quality characteristic compared between the synthetic scan plane image and the acquisition image frames. Additionally or alternatively, select quality characteristics may be defined to be of primary interest in connection with certain planes. For example, in a fetal CNS examination protocol, in connection with a TTP plane, a first quality characteristic may be defined to relate to saturation. In connection with the MSP plane, a third quality characteristic related to blurring may be defined to be of primary interest. As non-limiting examples, various protocols have other quality characteristics of importance, such as depth of acquisition, saturation due to gain, time-gain-compensation, frequency of resolution for a given feature, symmetry of image/anatomical structures, presence of particular combinations of anatomical structures and the like.

Additionally or alternatively, the QCM module 133 may be configured to define a tolerance range for one or more of the quality characteristics. The tolerance range for an individual quality characteristic may be predefined. Additionally or alternatively, tolerance range for an individual quality characteristic may be updated or calculated based on a variability of the corresponding quality characteristic across the plurality of acquisition image frames collected in connection with a scanning session for an individual patient. For example, a series of acquisition image frames may be analyzed by the QCM module 133 to identify the level or degree of blurriness in each acquisition image frame. For example, on a scale of 1-10, one series of acquisition image frames may exhibit a level or degree of blurriness that ranges between 2-3. In the foregoing example, when a synthetic scan plane image is generated by the GMA module 131, the synthetic scan plane image would have a corresponding blurriness quality characteristic with a level between 2-3. The QCM module 133 may assign levels to the quality characteristics in various manners. For example, the QCM module 133 may include one or more deep neural networks and/or utilize any suitable form of deep learning processing functionality for scoring the quality characteristics and/or combining weighted factors to provide a quality characteristic metric (e.g., a some of various quality characteristics multiplied by corresponding weights).

The signal processor 119 may be configured to provide various types of outputs and perform various actions based on the determination by the QCM a module 133 as to whether the synthetic scan plane image exhibits a quality common with the quality of the acquisition image frames. For example, the signal processor 119 may direct the display system 123 to, among other things, display the acquisition image frames, synthetic scan plane image and other information. Additionally or alternatively, the signal processor 119 may provide through the display system 123 user guidance instructions to direct the user to take one or more actions. For example, the instructions may direct the user to change the gain or other scan acquisition parameters of the ultrasound system. A general recommendation to simply change the gain and/or other scan acquisition parameters may be provided. Additionally or alternatively, a more detailed recommendation to change the gain and/or other scan acquisition parameters may be provided such as to change the gain or other parameter by an amount that is based on or related to an amount of difference between the acquisition image frames and the synthetic scan plane image. Additionally or alternatively, the signal processor 119 may be configured to provide user guidance information regarding at least one of position and orientation information for a scan plane for a future image frame to be acquired. Optionally, the user guidance information my include the following: i) provide a quality score of acquisition or protocol completeness, ii) provide guidance or automatically tune acquisition settings, iii) provide probe guidance, iv) provide explanations for why the reference scan plane is preferred and optionally provide quality scores to measure user required scan planes relative to a reference scan plane. The user guidance information my include real-time acquisition quality, protocol completeness, guidance for acquisition settings, explain-ability and probe manipulation.

The methods and systems herein provide an automated manner for identifying a synthetic scan plane which afford advantages over human operators. Among other advantages, the automated methods and systems herein guide novice users to understand termination criteria for a scanning session or alert users to the necessity to change settings to obtain a desirable scan plane. Additionally or alternatively, the automated methods and systems herein accelerate workflow for expert users. In accordance with new and unique aspects herein, information is presented on the display system 123 to the user that attempts to avoid an inexperienced user from obtaining initial acquisition image frames that have poor quality (e.g., as a result of improperly positioning the ultrasound probe or using nonideal scan parameters), seeing a synthetic scan plane image and concluding that the initial acquisition image frame is good enough. For example, the user might compared to the synthetic scan plane image to the acquisition image frame and conclude that the differences in quality are too minor to warrant further examination or further attempts to improve the acquisition image frame and save the acquisition image frame, even though with a few more adjustments to the probe position and/or acquisition settings, a significantly better image frame could be obtained. To address the foregoing concern, the signal processor 119 may "lockout" or otherwise prevent the user from selecting and saving the current acquisition image frame as the final image frame. Additionally or alternatively, user guidance information may be displayed to the user indicating that the present acquisition image frame has sufficiently lower quality than could potentially be obtained with minor adjustments, and provide a recommendation that the user continue to attempt to obtain a better acquisition image frame. Additionally or alternatively, the user guidance information may offer more specific suggestions in connection with changes to be made, such as changes in the position/orientation of the probe and/or changes in the acquisition parameters. For example, the user guidance information may indicate that the present image exhibits a 15% more blurring quality than would otherwise be present in an image frame acquired along they synthetic scan plane. As another example, the user guidance information may indicate that the present image has a shadowing quality level of 4 (e.g., on a scale of 0 to 10), whereas a shadowing quality level of 2 could be achieved with changes in the position/orientation of the probe or changes in the acquisition parameters. As yet further example, the user guidance information may indicate that a saturation level of the acquisition scan frame could be reduced by X, if the time gain compensation acquisition parameter were adjusted by an amount Y. Other outputs and actions are described herein.

Figure 2:
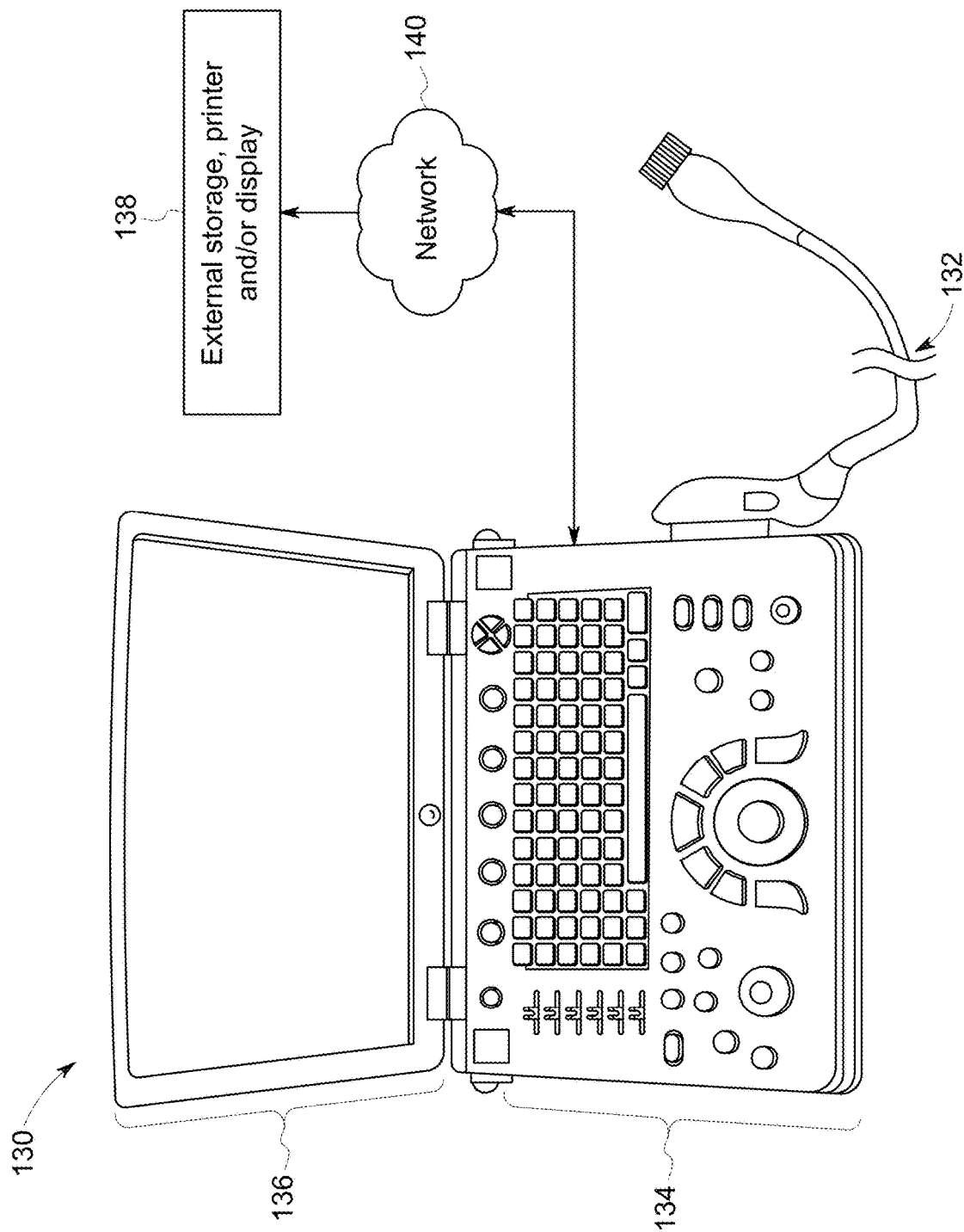
FIG. 2 illustrates a 3D-capable miniaturized ultrasound system configured to implement embodiments herein.

FIG. 2 illustrates a 3D-capable miniaturized ultrasound system 130 having a probe 132 that may comprise elements 106. The probe 132 may be configured to acquire 3D ultrasonic data. For example, the probe 132 may have a 2D array of transducer elements 104. A user interface 134 (that may also include an integrated display 136) is provided to receive commands from an operator.

As used herein, "miniaturized" means that the ultrasound system 130 is a handheld or hand-carried device or is configured to be carried in a person's hand, pocket, briefcase-sized case, or backpack. For example, the ultrasound system 130 may be a hand-carried device having a size of a typical laptop computer, for instance, having dimensions of approximately 2.5 inches in depth, approximately 14 inches in width, and approximately 12 inches in height. The ultrasound system 130 may weigh about ten pounds, and thus is easily portable by the operator. The integrated display 136 (e.g., an internal display) is also provided and is configured to display a medical image.

The ultrasonic data may be sent to an external device 138 via a wired or wireless network 140 (or direct connection, for example, via a serial or parallel cable or USB port). In some embodiments, external device 138 may be a computer or a workstation having a display. Alternatively, external device 138 may be a separate external display or a printer capable of receiving image data from the hand carried ultrasound system 130 and of displaying or printing images that may have greater resolution than the integrated display 136. It should be noted that the various embodiments may be implemented in connection with a miniaturized ultrasound system having different dimensions, weights, and power consumption. The external device 138 may implement all or part of the GMA and QCM modules 131, 133 and the generative models 127 (FIG. 1).

Figure 3:
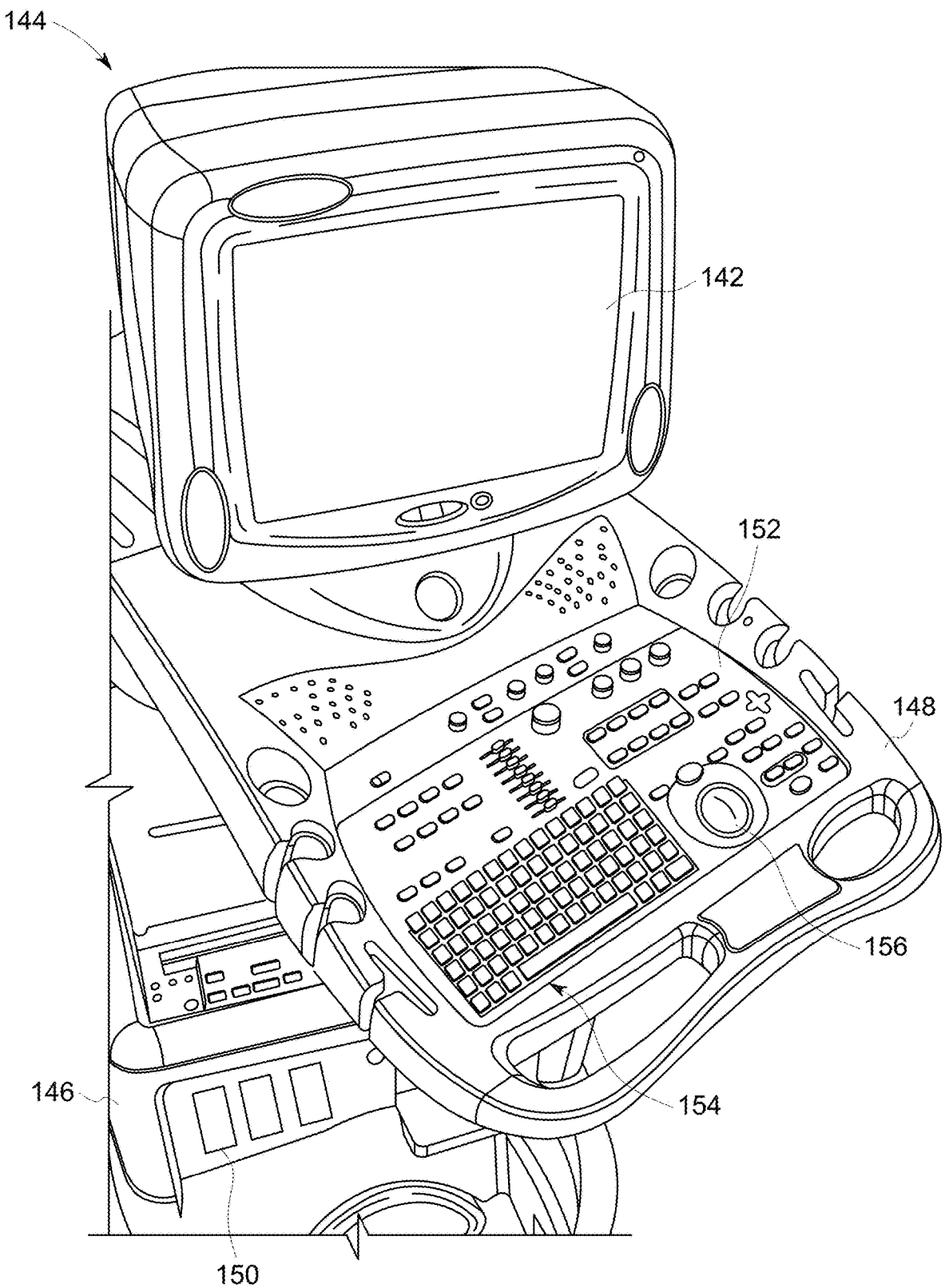
FIG. 3 illustrates a mobile ultrasound imaging system provided on a movable base configured to implement embodiments herein.

FIG. 3 illustrates a mobile ultrasound imaging system 144 provided on a movable base 146. The ultrasound imaging system 144 may also be referred to as a cart-based system. A display 142 and user interface 148 are provided and it should be understood that the display 142 may be separate or separable from the user interface 148. The system 144 has at least one probe port 150 for accepting probes (not shown) that may have elements 106 that comprise single crystal material as discussed herein.

The user interface 148 may optionally be a touchscreen, allowing the operator to select options by touching displayed graphics, icons, and the like. The user interface 148 also includes control buttons 152 that may be used to control the system 144 as desired or needed, and/or as typically provided. The user interface 148 provides multiple interface options that the user may physically manipulate to interact with ultrasound data and other data that may be displayed, as well as to input information and set and change scanning parameters. The interface options may be used for specific inputs, programmable inputs, contextual inputs, and the like. For example, a keyboard 154 and track ball 156 may be provided.

Figure 4:
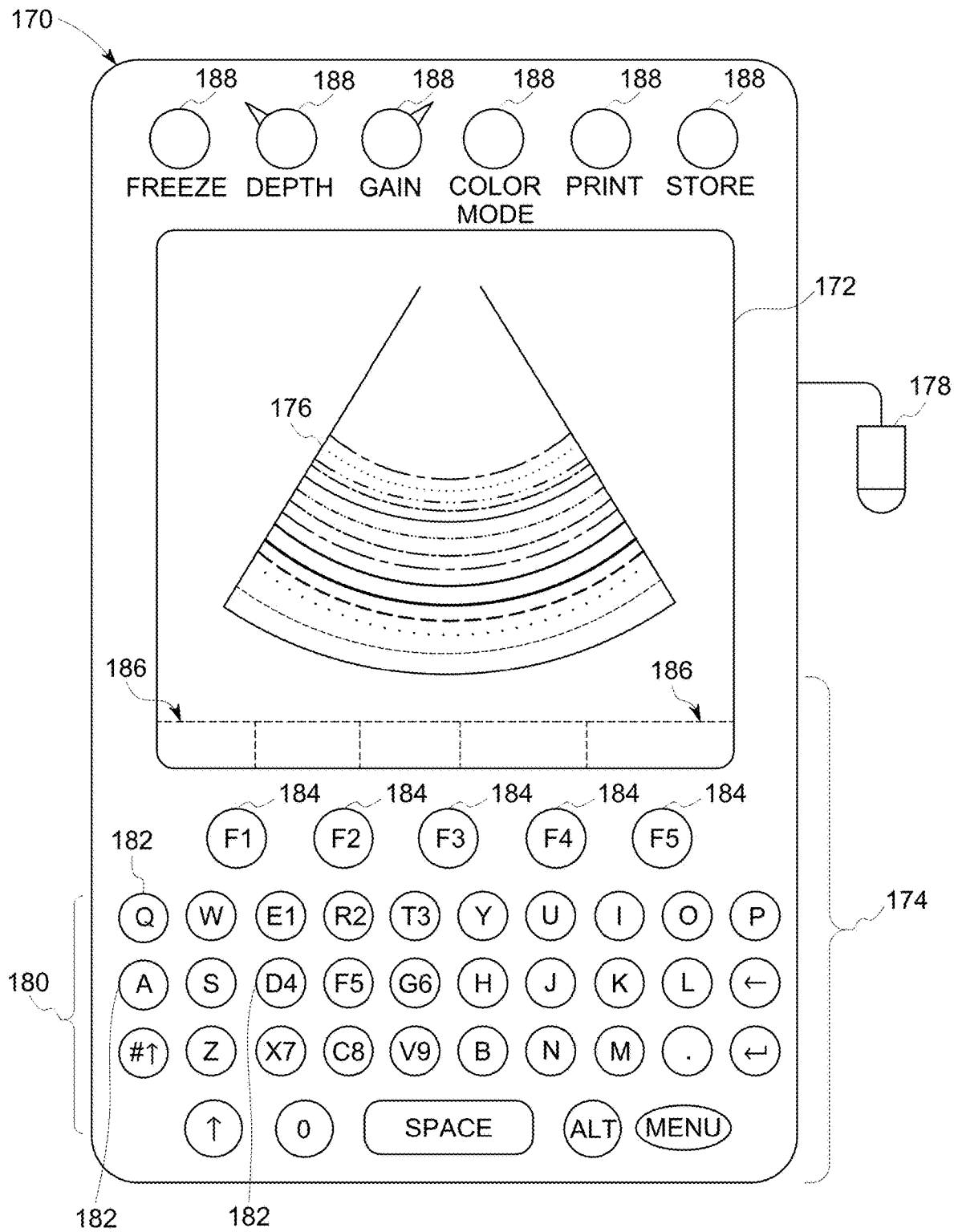
FIG. 4 illustrates a hand carried or pocket-sized ultrasound imaging system wherein the display and user interface form a single unit configured to implement embodiments herein.

FIG. 4 illustrates a hand carried or pocket-sized ultrasound imaging system 170 wherein display 172 and user interface 174 form a single unit. By way of example, the pocket-sized ultrasound imaging system 170 may be approximately 2 inches wide, approximately 4 inches in length, and approximately 0.5 inches in depth and weighs less than 3 ounces. The display 172 may be, for example, a 320×320 pixel color LCD display (on which a medical image 176 may be displayed). A typewriter-like keyboard 180 of buttons 182 may optionally be included in the user interface 174. The system 170 is connected to a probe 178 that has transducer elements 106 comprising a single crystal material as discussed herein. Multi-function controls 184 may each be assigned functions in accordance with the mode of system operation. Therefore, each of the multi-function controls 184 may be configured to provide a plurality of different actions. Label display areas 186 associated with the multi-function controls 184 may be included as necessary on the display 172. The system 170 may also have additional keys and/or controls 188 for special purpose functions, which may include, but are not limited to "freeze," "depth control," "gain control," "color-mode," "print," and "store."

Examination Protocols

By way of example, embodiments herein may define generative models that are uniquely tailored to generate synthetic scan planes and SSP images in connection with implementing a fetal CNS examination protocol. Central nervous system (CNS) malformations are a common congenital abnormalities. The ultrasound fetal CNS examination may be used to help diagnose fetal CNS anomalies. By way of example, the fetal CNS protocol may involve collecting US data for a collection of image frames along chosen standard 2D planes through the central nervous system of a fetus. For example, the user selected scan planes for a fetal CNS examination protocol may include the Trans-Cerebellar Plane (TCP), the Trans-Thalamic Plane (TTP), and the Trans-Ventricular Plane (TVP). Additionally or alternatively, the fetal CNS examination protocol may provide that a 3D US data set is acquired for a volume including the fetal CNS region of interest. When a 3D US data set is acquired, in addition to the TCP, TTP, and TVP chosen scan planes, the protocol may also define a chose scan plane to be the Median or Mid-Sagittal Plane (MSP) to add another clinically useful perspective.

The orientation of the Mid-Sagittal Plane provides a unique view of the intracranial structures such as the corpus callosum (CC) and an axial view of the cerebellar vermis (CV). For example, the observation from the MSP facilitates clinical diagnosis of Agenesis of the Corpus Callosum (ACC) and Dandy-Walker Syndrome. However, it is difficult to obtain US data along the MSP scan plane that provides an MSP image frame with sufficient quality, due to various imaging conditions such as poor fetal position, acoustic shadowing, and the user scanning skills. Due to the difficulties in acquiring US data of sufficient quality along the MSP scan plane, heretofore, in some instances, clinicians would only conduct indirect examination based on several transverse planes of the fetal brain in many cases, which could lead to misdiagnosis of the CC or CV related diseases.

TCP, TTP, and TVP are the important planes in a fetal CNS examination. The anatomic landmarks in these planes include the cavum septi pellucidi (CSP), thalami, cerebellum, cisterna magna, and lateral ventricles. In addition to observing the morphology of these structures, measurements of this anatomy is also important to prenatal ultrasonography. The standard measurements of the fetal head include the head circumference (HC), biparietal diameter (BPD), and occipitofrontal diameter (OFD) from the TTP. The width of the cisterna *magna* (CM) and trans-cerebellar diameter (TCD) are obtained from the TCP and the width of the lateral ventricles (LVW) from the TVP.

Today, 3D ultrasound has been widely accepted for fetal imaging and the major advantage is the ability to obtain many views from one volumetric dataset. However, many physicians have not yet adopted the use of 3D acquisition in practice due to a lack of knowledge required for 3D acquisition versus 2D imaging, the difficulty in recognizing some views of the anatomy from a totally unfamiliar display such as the C Plane, and the need to learn new methods for rotating, translating, and manipulating the 3D volumes. Therefore, a faster and more user-friendly method to automatically inform the user when the "best" acquisition scan planes have been obtained in a fetal CNS examination could significantly boost both the quality and efficiency of clinical diagnosis.

As another example, a protocol may involve examining one or more organs, such as a kidney examination, liver examination, gallbladder examination and the like. By way of example, the protocol for a kidney examination may call for the acquisition of image frames along a long axis scan plane and a transverse scan plane of the upper poles, mid portions and the lower poles of the kidney. The kidney examination protocol may also call for acquisition of image frames along the long axis scan plane and transverse scan plane for the cortex and renal pelvis. Maximum measurements of renal length are recorded for both kidneys. When practical, renal echogenicity may be compared to the echogenicity of the adjacent liver or spleen. It is recognized that the foregoing is only one example of some of the image frames that may be acquired along certain acquisition scan planes in connection with a kidney examination protocol.

While the illustrations generally show the B-mode ultrasound images, it is recognized that embodiments herein may be applied to other types of ultrasound examinations, such as in connection with power Doppler image frames, shear wave image frames and the like. For example, Doppler imaging may be utilized to examine vasculature of an organ of interest, such as the liver, kidneys, gallbladder, as well as the cardiac system, such as a heart, cardiovascular system and the like.

Process to Manage Acquisition Quality

Figure 5:
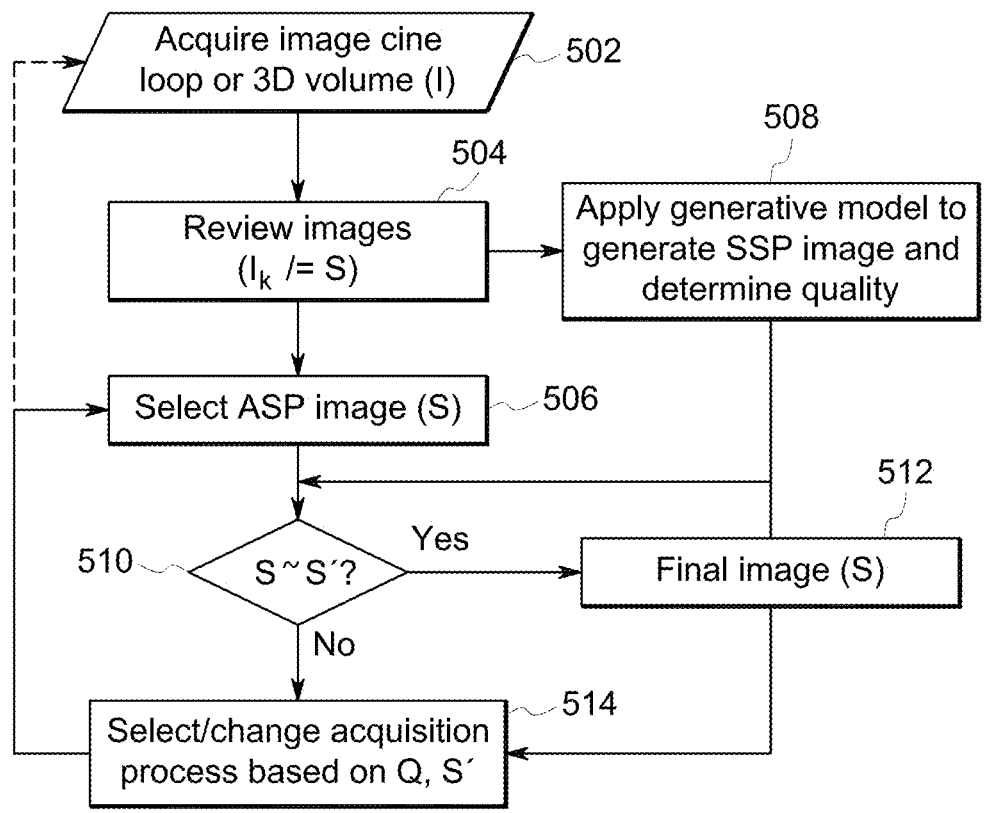
FIG. 5 illustrates a process implemented in accordance with embodiments herein to manage acquisition quality.

FIG. 5 illustrates a process implemented in accordance with embodiments herein to manage acquisition quality. At 502, the ultrasound system acquires ultrasound data, utilizing the transducer elements of a probe, wherein the ultrasound data is collected along multiple acquisition scan planes in connection with collection of image frames to form a cine loop (I) and/or 3-D volume. By way of example, multiple image frames may be collected along each acquisition scan plane within a set of acquisition scan planes, such as to illustrate movement within the anatomy of interest along the individual acquisition scan planes within the set. Additionally or alternatively, during a 3-D volume acquisition, the ultrasound data may be collected along a number of acquisition scan planes sufficient to define a collection of image frames for a volumetric data set.

At 504, the user of the ultrasound system reviews all or a portion of the image frames acquired at 502. At 506, the user of the ultrasound system selects one or more of the acquisition image frames oriented along a corresponding one or more acquisition scan planes.

Optionally, the acquiring, reviewing and selecting operations at 502-506 may be iteratively performed. For example, a first subset of image frames (e.g., in connection with the user attempting to acquire a preferred or best image frame along one particular scan plane) may be acquired at 502. The subset of image frames may be reviewed at 504 and the user may select one of the image frames from the subset at 506. Thereafter, the operations at 502 to 506 may be repeated in connection with a second scan plane, and then a third scan plane, etc. As a nonlimiting example, in connection with a fetal CNS examination protocol, the operations at 502-506 may be implemented in an effort to collect a preferred or best image frame along one of the TCP plane, TTP plane, TVP plane and MSP plane. Next, the operations at 502-506 may be repeated in an effort to collect a preferred or best image frame along another one of the TCP plane, TTP plane, TVP plane and MSP plane, and then along another one of the TCP plane, TTP plane, TVP plane and MSP plane, until the user has collected, based on the users best efforts, a candidate preferred or best image frame along each of the TCP plane, TTP plane, TVP plane and MSP plane.

Each of the image frames within the cine loop have certain characteristics that define the quality of the corresponding image frame. In general, image frames within a single cine loop or 3-D volume will exhibit the same or substantially similar values for the quality characteristics. For example, when a cine loop of image frames is acquired while holding a probe at a single position and orientation, the collection of image frames would exhibit a common or substantially similar degree of blurriness, level of shadows, saturation and other quality characteristics. As another example, when a collection of image frames are acquired for a three-dimensional volume, the collection of image frames would similarly exhibit a common or substantially similar degree of blurriness, level of shadows, saturation and other quality characteristics. The synthetic scan plane image has a common image quality as the image quality of the plurality of image frames reviewed at 504. Successive image frames (e.g., image frames in a single cine loop or image frames in a 3-D volume) will have a common image quality (or image quality within a tolerance range), at least with respect to the quality characteristics of interest.

At 508, the processor applies a generative model to at least one of the US data or the plurality of the image frames to generate a synthetic scan plane image along an estimated or projected synthetic scan plane. The generative model may utilize the entire US data set and/or a subset when generating the synthetic scan plane image. Additionally or alternatively, the generative model may utilize all of the available image frames and/or a subset of the available image frames to generate the synthetic scan plane image. The generative model is defined based on a training ultrasound data set as explained herein. The synthetic scan plane image has a common image quality as the image quality of the plurality of image frames utilized by the generative model to identify the synthetic scan plane and corresponding synthetic scan plane image. It is recognized that one or more of the quality characteristics of interest may vary within an acceptable tolerance range between the synthetic scan plane image and the plurality of image frames, but still be considered to exhibit a common image quality.

At 510, the processor compares the acquisition image frames selected at 506 and the synthetic scan plane image automatically determined at 508 for similarities and differences in one or more of the quality characteristics of interest. The values for the quality characteristics for the acquisition image frames are depend, in part, on an experience level of the operator. Novice users may perform an unduly long scan in an effort to continuously attempt to locate an acquisition scan plane that affords an image frame with a preferred or optimal quality. Performing unduly long scans is also referred to as overestimating a potential scan plane. Alternatively, a novice user may terminate acquisition unduly early by incorrectly concluding that the operator has already obtained image frames along the preferred or best scan plane that would afford the preferred for best image quality available. Terminating an acquisition session unduly early is also referred to as underestimating a potential scan plane.

The user selects acquisition scan planes and associated image frames with respect to individual patient examinations based on what the user estimates to be the preferred or best quality of image frames that are attainable. The acquisition scan planes and related image frames for each patient have different corresponding qualities. Therefore, the selections and estimations by the user represent a general abstraction of what the user expects to acquire and is unquantifiable, thereby preventing the knowledge to be standardized. The quality associated with the acquisition scan plane selected by the user is typically not computed in prior systems. To the extent that prior systems attempted to quantify a quality associated with user selected acquisition scan planes, the prior systems were only able to perform the computation based on broad metrics, such as edges, contrast and the like. The quality associated with user selected scan planes in the past was not task specific, namely the quality did not take in consideration the particular anatomy or type of examination.

In accordance with new and unique aspects herein, the generative model is utilized to assist novice or less experienced operators, and to reduce demand or load on all types of users. Additionally, utilizing the generative model provides an adaptable termination point for an examination, by determining whether a preferred or optimal acquisition scan plane has already been utilized to acquire image frames or alternatively whether a preferred or optimal scan plane has not yet been utilized, and thus better image frames may still be attained. By determining the termination point, embodiments herein reduce scan time and facilitate obtaining image frames along a scan plane having at least a certain level of quality. Embodiments herein further provide an adaptable and quantified metric for determining whether to change an acquisition process or to select a particular acquisition process.

At 510, when the quality characteristics of an image frame from a user selected acquisition scan plane are similar, or within a predefined tolerance, to the quality characteristics of the synthetic scan plane image, flow moves to 512. At 512, the processor may inform the user that the selected image frame represents a preferred or best quality that can be obtained by the imaging system for the current patient. Additionally or alternatively, the processor informs the user that the acquisition scan plane selected by the user represents a preferred or best scan plane that can be obtained by the imaging system for the current patient. Optionally, the user selected acquisition image frame is utilized as the final images. By informing the user that the selected image frame and/or acquisition scan plane represents a preferred or best scan plane that can be obtained by the imaging system for the current patient, in accordance with new and unique aspects herein, embodiments prevent unduly excessive scan operations. Embodiments prevent the user from attempting to remove shadows that cannot be removed and will remain in any image frames regardless of the scan plane. Embodiments also instill more confidence in a user through affirmation that the user has obtained acquisition image frames that are as good as possible for the user imaging system, protocol and patient.

Alternatively, at 510, when the quality characteristics of the user selected scan plane differ, by a predefined amount, from the quality characteristics of the synthetic scan plane, flow moves to 514.

It is recognized that the decision at 510 may be applied to one or more image frames and corresponding one or more synthetic scan plane images. For example, first quality characteristics for an acquisition image frame along an acquisition TCP plane may be compared to corresponding quality characteristics for a synthetic scan plane image along a synthetic TCP plane. The same or different second quality characteristics for an acquisition image frame along an acquisition TTP plane may be compared to corresponding quality characteristics for a synthetic scan plane image along a synthetic TTP plane.

Additionally or alternatively, the same or different levels for and/or types of quality characteristics may be applied in connection with different scan planes, such as when different quality characteristics have a greater impact on the analysis and measurements along particular scan planes or are more/less likely to be present. For example, a shadowing characteristic may be an important quality characteristic (or more likely to be present) in connection with image frames along the TCP and TTP planes, whereas shadowing is a less important quality characteristic (or less likely to be significant) for image frames along the TVP plane. As another example, a blurring characteristic may be an important quality characteristic (or common problem) in connection with image frames along the TVP and MSP planes, whereas blurring is a less important quality characteristic (or not common) for image frames along the TCP and TTP planes.

At 514, the processor may implement multiple or alternative actions. For example, at 514, the processor may provide user guidance information regarding settings for at least one of i) scan acquisition parameters, and/or ii) position and orientation information for a scan plane for a future image frame to be acquired. When an instruction is provided to change gain or another scan acquisition parameter, the suggestion may include a general suggestion (e.g., "The time gain compensation may be too high") and/or the suggestion may also include a recommended amount for the change. The user guidance information may also provide the following: i) provide a quality score of acquisition or protocol completeness, ii) provide guidance or automatically tune acquisition settings, iii) provide probe guidance, iv) provide explanations for why the reference scan plane is preferred and optionally provide quality scores to measure user required scan planes relative to a reference scan plane, real-time acquisition quality, protocol completeness, guidance for acquisition settings, explain-ability and probe manipulation. The methods and systems herein provide an automated manner for identifying a synthetic scan plane which afford advantages over human operators. Among other advantages, the automated methods and systems herein guide novice users to understand termination criteria for a scanning session or alert users to the necessity to change settings to obtain a desirable scan plane. Additionally or alternatively, the automated methods and systems herein accelerate workflow for expert users.

Additionally or alternatively, at 514, the processor may allow the user to continue the acquisition in search of an acquisition image frame (and corresponding acquisition scan plane) that affords a level of quality for the quality characteristics that is similar to the quality of the synthetic scan plane image. The user may be allowed to continue to adjust the position and orientation of the US probe and/or adjust acquisition scanner setting until the user obtains an acquisition image frame of sufficient quality. Additionally or alternatively, the processor may establish a limited amount of time for the user to attempt to obtains an acquisition image frame of sufficient quality. Once the time expires, the processor may automatically provide guidance information and/or perform other actions.

Figure 6:
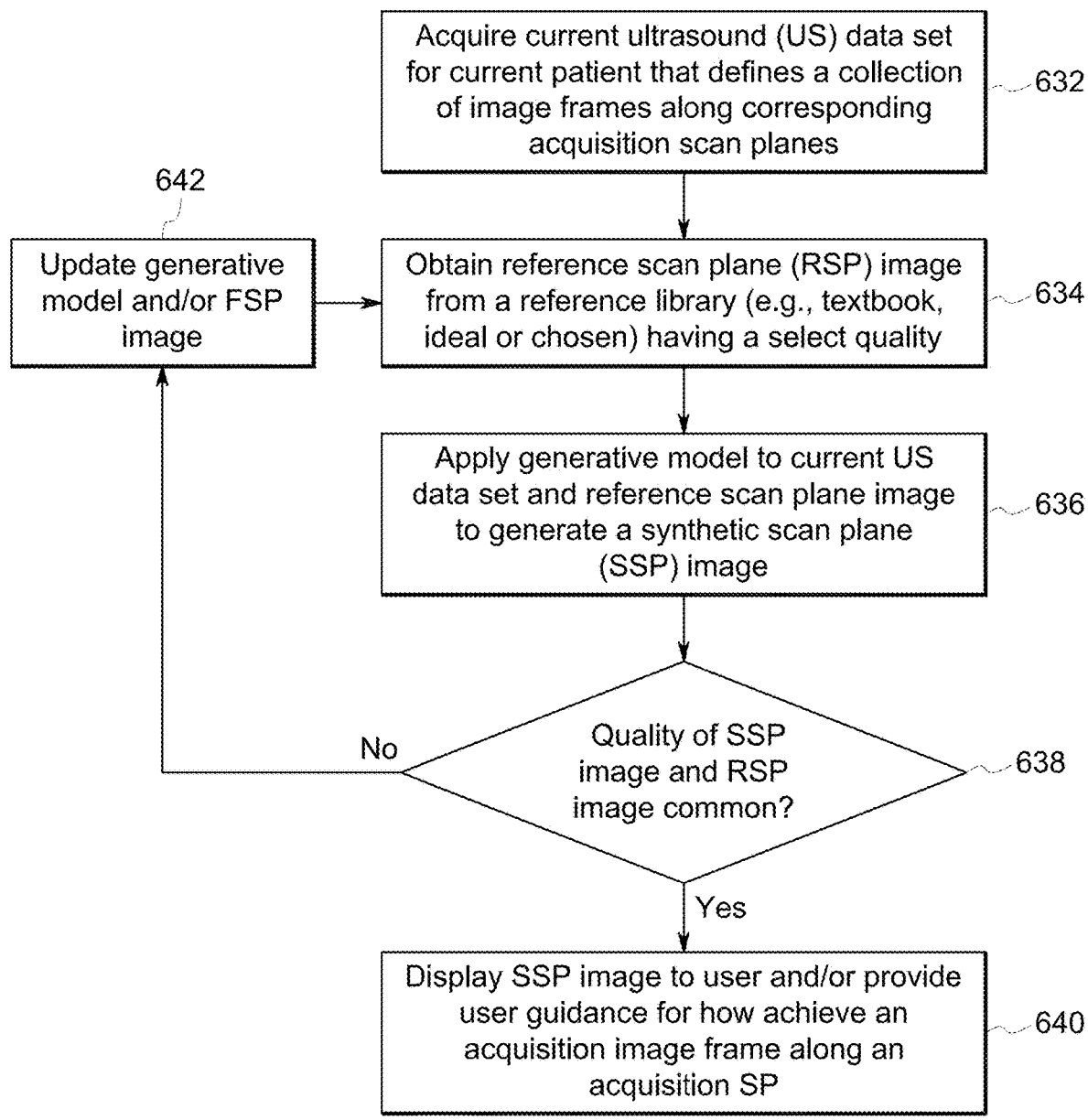
FIG. 6 illustrates a process for managing acquisition quality in accordance with an alternative embodiment.

FIG. 6 illustrates a process for managing acquisition quality in accordance with an alternative embodiment. At 632, the ultrasound system acquires ultrasound data, utilizing the transducer elements of a probe, wherein the ultrasound data is collected along multiple acquisition scan planes in connection with a collection of image frames. At 634, a processor obtains a reference scan plane (RSP) image from a reference library where the RSP image has a corresponding select quality. The operation at 634 may be omitted by a processor of the ultrasound system, or by a separate device, system, server and the like. The RSP image may represent a textbook, ideal or otherwise chosen image. For example, the RSP image may correspond to an acquisition scan plane image acquired during a separate examination of the same patient, a different patient or a patient population. Additionally or alternatively, the RSP image may represent an average or other mathematical combination of multiple acquisition scan plane images from examinations of a patient population.

At 636, the processor applies the RSP image to a generative model, along with a current ultrasound data set (acquired at 632) for the current patient. The generative model analyzes the ultrasound data set and seeks to generate a synthetic scan plane (SSP) image having a common quality as the RSP. For example, the RSP may have a certain limited level of blurriness (or no blurriness), a certain level of saturation (or no saturation), and little or no shadowing. The levels of blurring, saturation and shadowing in the RSP image are used to define a quality characteristic for which the generative model seeks to match when identifying the SSP.

At 638, the processor identifies the quality of the SSP image and compares the quality of the SSP image to the quality of the RSP image. When the qualities of the SSP and RSP images are common or within a defined tolerance range, flow moves to 640. Alternatively, when the qualities of the SSP and RSP images differ or differ by an amount outside of the tolerance range, flow moves to 642.

At 640, processor of the ultrasound system displays the SSP image to the user and/or provides user guidance for how to achieve an acquisition image frame along an acquisition scan plane corresponding to the synthetic scan plane. The processor may perform alternative or additional operations as described herein. At 642, various corrective actions may be taken when the quality of the SSP and RSP images are outside of the tolerance range. For example, at 642, the processor may update the generative model. For example, the processor may determine that an SSP image is not able to be generated from the current US data set that has a quality the same as the RSP image. For example, the current US data set may be collected from a patient that exhibits certain anatomical characteristics that prevent the SSP image from being generated with the same level or lack of shadowing as in the RSP image. At 642, in the foregoing example, the generative model may be updated to reflect that the best SSP image will have slightly more shadowing than in the RSP image. Additionally or alternatively, the FSP image may be updated based on the SSP image, such as to add the current patient to the patient population in the reference library. For example, the reference library may not have reference ultrasound data sets or reference scan plane images from a patient having the particular demographics of the current patient. According, at 642, the library is updated.

While the operations of FIG. 6B are described in connection with a real-time operation by an ultrasound system, it is recognized that at least the operations at 634-642 may be implemented through postprocessing utilizing various electronic devices other than an ultrasound system, such as a smart phone, tablet device, laptop computer, desktop computer, server and the like.

Figure 7:
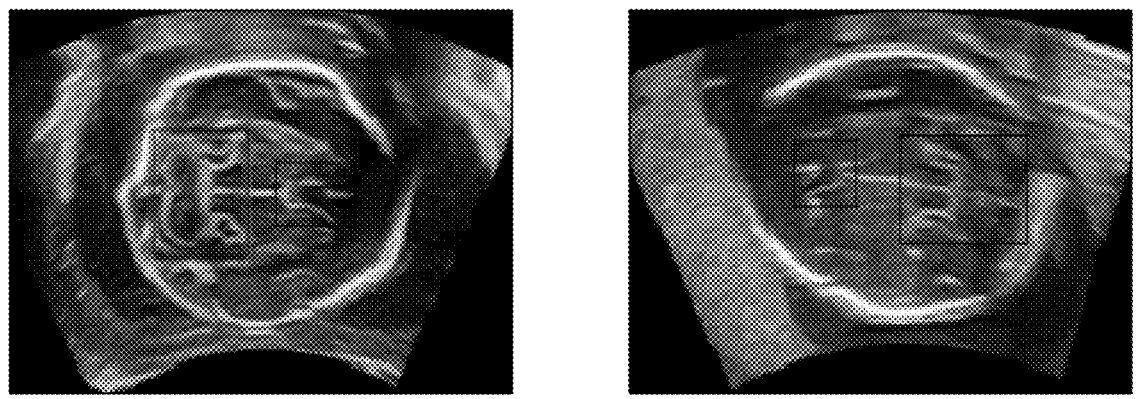
FIG. 7 illustrates an example of different qualities for image frames collected along different scanned planes.

FIG. 7 illustrates an example of different qualities for image frames collected along different scanned planes. The image frames of FIG. 7 were collected in connection with diagnostic examination of a trans-cerebral plane through a fetal central nervous system volume. Anatomies of interest such as the cerebellum and cavum septi pellucidi (CSP) are more clearly visible in the image frame in the first panel where the first image frame was collected in connection with a preferred scan plane. In the first panel, the image frame illustrates good acquisition quality with no motion blurring, very little shadows, and all of the anatomical features of interest are clearly visible.

The image frame in the second panel was collected along a different, undesirable scan plane which yielded poor acquisition quality. The image frame in the second panel was acquired along an undesirable scan plane which exhibited a difficult angle of acquisition for the features of interest. In addition, another characteristic of the poor acquisition quality is the fact that the image frame is blurry (e.g., due to probe movement or patient movement or both).

Figure 8A:
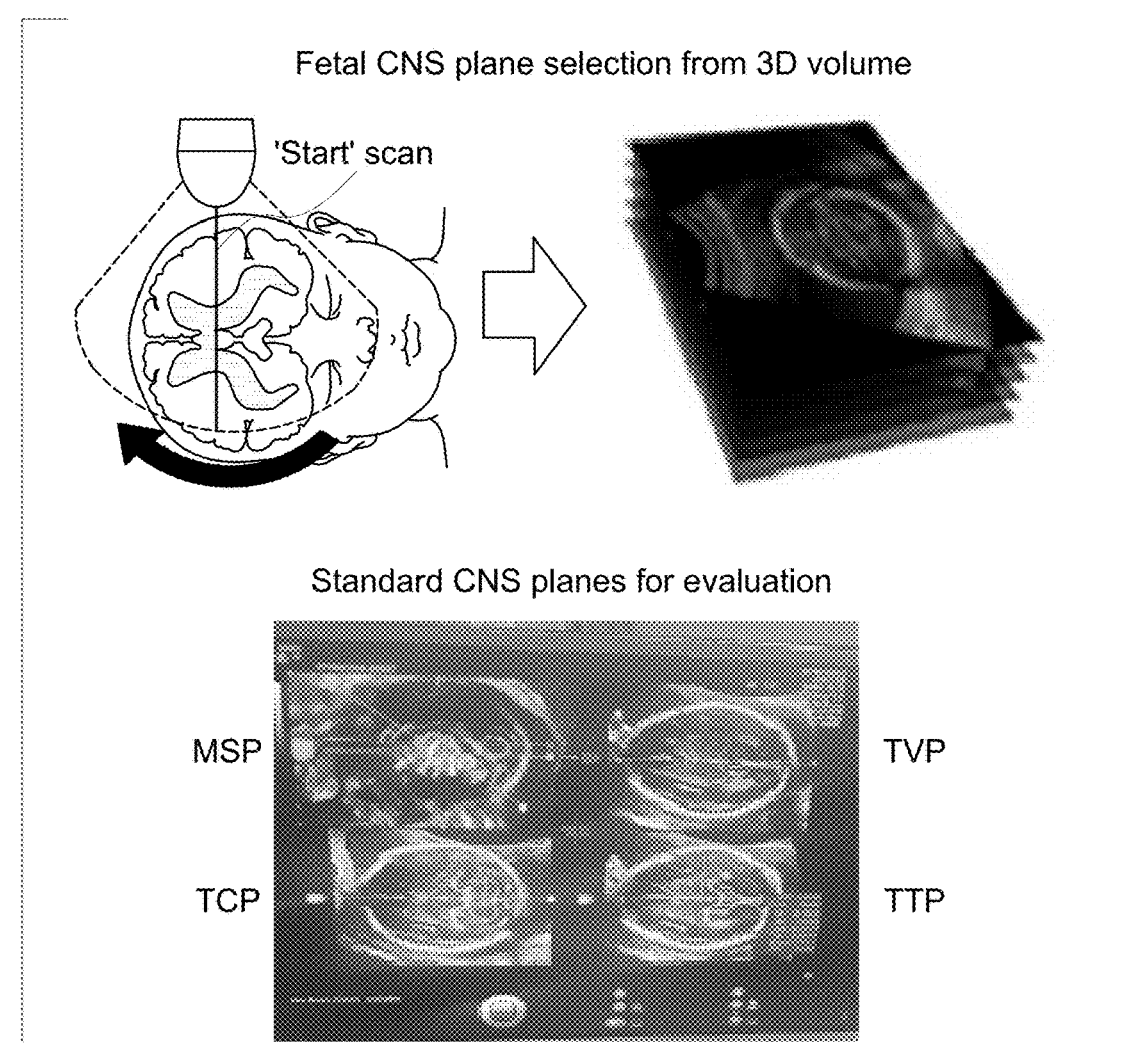
FIG. 8A illustrates an example of a diagnostic examination for a fetal central nervous system in accordance with embodiments herein.
Figure 8B:
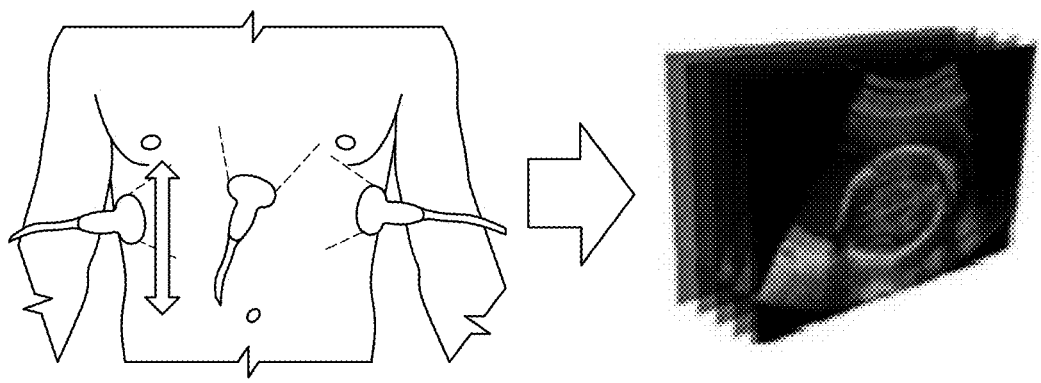
FIG. 8B illustrates an example of a diagnostic examination for one or more organs in accordance with embodiments herein.
Figure 8B:
Figure 8B:

FIGS. 8A and 8B illustrate graphical representation of example use cases. In the example of FIG. 8A, the diagnostic examination is for a fetal central nervous system examination. Ultrasound data is collected along multiple scan planes for a three-dimensional volume that includes a portion of the fetal CNS. The ultrasound data from the 3-D volume may be utilized to form a volume collection of image frames. A user selects one or more scan planes from the fetal CNS volumetric data set. FIG. 8A illustrates examples of standard CNS planes that are chosen for evaluation, such as the medial sagittal plane (MSP), the trans-cerebellar plane (TCP), the trans-ventricular plane (TVP), and the trans-thalamic plane (TTP). Image frames acquired along the standard CNS planes may be co-displayed in a 2×2 configuration, separately displayed or presented in various alternative manners.

In the example of FIG. 8B, the diagnostic examination is for an examination of one or more organs, such as the liver, kidney, gallbladder, etc. Ultrasound data is collected while moving the position and/or orientation of the probe to collect a 3-D volume of images. Additionally or alternatively, the probe may be maintained in a relatively stationary position and/or slightly rotated or translated, while collecting a series of image frames along a common scan plane or a relatively small number of closely spaced or closely oriented scan planes in a cine loop. The user selects one or more scan planes from the 3-D volume were the scan plane is selected in an effort to best illustrate a feature of interest.

Figure 9:
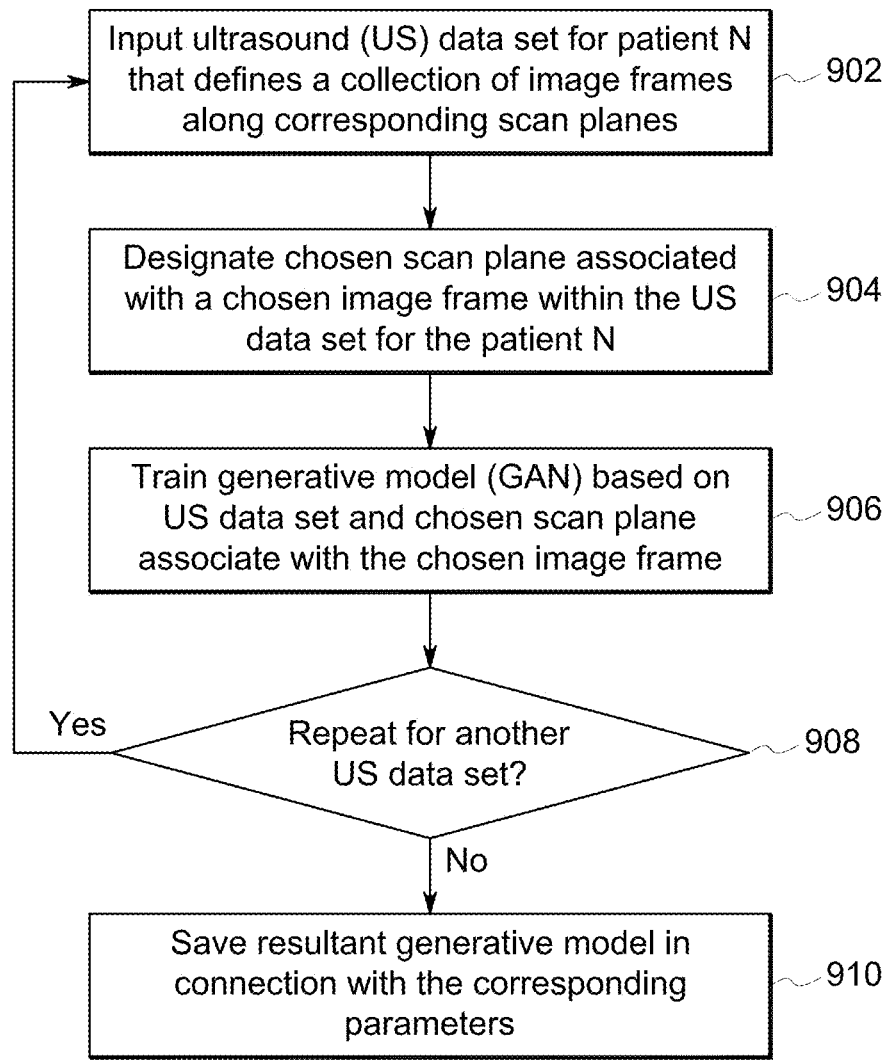
FIG. 9 illustrates a process for training a generative model in accordance with embodiments herein.

FIG. 9 illustrates a process for training a generative model in accordance with embodiments herein. The process of FIG. 9 may be implemented by one or more processors of an ultrasound system, or by various other computing systems, such as a smart phone, tablet device, laptop computer, workstation, remote server, medical records management system and the like.

At 902, the one or more processors receive an ultrasound data set for a particular patient N. The ultrasound data set corresponds to and defines a collection of image frames that were acquired along a single scan plane and/or a collection of scan planes, such as when acquiring a three-dimensional volumetric data set and/or a cine loop at one scan plane and/or a limited set of scan planes.

At 904, the one or more processors receive a designation for one or more "chosen" scan planes. The chosen scan plane may represent a best or optimal scan plane that should be chosen for the corresponding collection of image frames in order to yield a chosen or optimal image frame from the ultrasound data set for the current patient N. additionally or alternatively, the designation at 904 may include a designation of multiple scan planes, such as the MSP, TCP, TVP and TTP scan planes associated with a fetal CNS examination protocol. As another example, when the examination protocol concerns examining an organ of interest, such as the liver, kidney, gallbladder, the designation of the chosen/optimal scan plane may indicate a view of a mid-cross-section of a kidney/gallbladder for evaluation of volume or for presence of stones.

Additionally or alternatively, at 904, further information concerning the US data set may be entered, such as a designation of a protocol that was followed in connection with the collection of the US data set, the acquisition settings for the ultrasound system, designators for the chosen scan plane(s), patient demographic information (e.g., height, weight, age, sex, smoking history) and the like. By way of example, the protocol may indicate that the US data set was collected in connection with a fetal CNS examination, an organ or other anatomy to be examined, and the like.

At 906, the one or more processors train the generative model based on the US data set and designated chosen scan plane. By way of example, the GAN may be trained using deep learning methods such as deep convolutional neural networks. One challenge in training a GAN is to maintain stability as the training process can be inherently unstable, resulting in simultaneous dynamic training of two competing models.

Closing Statements

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

Aspects are described herein with reference to the Figures, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A system, comprising:
a transducer with piezoelectric transducer elements configured to collect ultrasound (US) data;
memory configured to store program instructions;
a processor configured to:
acquire the US data, utilizing the transducer elements, along one or more acquisition scan planes, the US data defining a plurality of image frames that have a first image quality; and
apply a generative model to at least one of the US data or plurality of image frames to generate a synthetic scan plane image along a synthetic scan plane, wherein the generative model is defined based on one or more training ultrasound data sets, the synthetic scan plane image having an image quality that is common with the first image quality of the plurality of image frames; and
a display configured to display the synthetic scan plane image,
wherein the synthetic scan plane image does not correspond to any scan planes associated with any of the plurality of acquisition image frames.

2. The system of claim 1, wherein the processor is further configured to predict the synthetic scan plane image based on a generative adversarial network model.

3. The system of claim 1, wherein the processor is further configured to repeat the acquire and apply to adaptively identify a new synthetic scan plane image based on new acquisition image frames image frames.

4. The system of claim 1, wherein the generative model applies acquisition parameters to identify the synthetic scan plane image.

5. The system of claim 1, wherein the processor is further configured to provide user guidance information to change gain or other scan acquisition parameter based on differences between the synthetic scan plane image and the plurality of image frames.

6. The system of claim 1, wherein the processor is further configured to provide user guidance information regarding at least one of position or orientation information for a scan plane for a future image frame to be acquired.

7. The system of claim 1, wherein the processor is implemented in at least one of an ultrasound system, a smart phone, tablet device, laptop computer, desktop computer or server.

8. A method, comprising:
utilizing a transducer to transmit ultrasound signals and receive ultrasound (US) data from a region of interest, wherein the US data is acquired along one or more acquisition scan planes, the US data defining a plurality of image frames that have a first image quality;
obtaining a reference scan plane image;
applying a generative model to at least one of the US data or plurality of image frames to generate a synthetic scan plane image along a synthetic scan plane, wherein the generative model is defined based on one or more training ultrasound data sets, the synthetic scan plane image having an image quality that is common with the first image quality of the plurality of image frames;
comparing a quality of the reference scan plane image to a quality of the synthetic scan plane image, and
based on the quality of the reference scan plane image being within a defined tolerance range of the quality of the synthetic scan plane image, displaying the synthetic scan plane image.

9. The method of claim 8, wherein the applying includes predicting the synthetic scan plane image based on a generative adversarial network model.

10. . The method of claim 8, wherein the synthetic scan plane image does not correspond to any scan planes associated with any of the plurality of acquisition image frames.

11. The method of claim 8, further comprising repeating the acquiring and the applying to adaptively identify a new synthetic scan plane image based on new acquisition image frames image frames.

12. The method of claim 8, further comprising providing user guidance information to change gain or other scan acquisition parameter based on differences between the synthetic scan plane image and the plurality of image frames.

13. The method of claim 8, further comprising obtaining the reference scan plane image, from a reference library, to the generative model and utilizing the reference scan plane image to generate the synthetic scan plane image with the image quality of the synthetic scan plane image being common with a quality of the reference scan plane image.

14. The method of claim 8, wherein the common image quality is defined by at least a first quality characteristic, the method further comprising defining a tolerance range for the first quality characteristic based on a variation of the first quality characteristic across the plurality of image frames, the generative model providing the reference frame with the first quality characteristic within the tolerance range.

15. The method of claim 8, wherein diagnostic information is not derived directly from the synthetic scan plane, the diagnostic information derived from the plurality of image frames.

16. The method according to claim 8, wherein the reference scan plane image is obtained from a different patient than the US data.

17. The method according to claim 8, wherein the reference scan plane image is obtained from a separate examination than the US data.

18. A computer program product comprising a non-signal computer readable storage medium comprising computer executable code to:
obtain ultrasound (US) data from a region of interest, wherein the US data is acquired along one or more acquisition scan planes, the US data defining a plurality of image frames that have a first image quality;
obtain a reference scan plane image;
apply a generative model to at least one of the US data or plurality of image frames to generate a synthetic scan plane image along a synthetic scan plane, wherein the generative model is defined based on one or more training ultrasound data sets, the synthetic scan plane image having an image quality that is common with the first image quality of the plurality of image frames;
compare a quality of the reference scan plane image to a quality of the synthetic scan plane image; and
based on the quality of the reference scan plane image being within a defined tolerance range of the quality of the synthetic scan plane image, display the synthetic scan plane image.

19. The computer program product of claim 18, wherein the computer executable code is further configured to apply includes predicting the synthetic scan plane image based on a generative adversarial network model.

20. The computer program product of claim 18, wherein the common image quality is defined by at least a first quality characteristic and wherein the computer executable code is further configured to define a tolerance range for the first quality characteristic based on a variation of the first quality characteristic across the plurality of image frames, the generative model providing the reference frame with the first quality characteristic within the tolerance range.

21. The computer program product of claim 18, wherein the computer executable code is further configured to provide user guidance information to at least one of: i) change gain or other scan acquisition parameter based on differences between the synthetic scan plane image and the plurality of image frames; or ii) at least one of position or orientation information for a scan plane for a future image frame to be acquired.

* * * * *